(12) United States Patent
Bardy et al.

(10) Patent No.: US 6,647,292 B1
(45) Date of Patent: Nov. 11, 2003

(54) UNITARY SUBCUTANEOUS ONLY IMPLANTABLE CARDIOVERTER-DEFIBRILLATOR AND OPTIONAL PACER

(75) Inventors: Gust H. Bardy, Seatlle, WA (US); Riccardo Cappato, Ferrara (IT)

(73) Assignee: Cameron Health, SanClemente, CA (US)

( * ) Notice: Subject to any disclaimer, the term of this patent is extended or adjusted under 35 U.S.C. 154(b) by 282 days.

(21) Appl. No.: 09/663,606

(22) Filed: Sep. 18, 2000

(51) Int. Cl.$^7$ ................................................ A61N 1/39
(52) U.S. Cl. ................ 607/5; 607/4; 607/36; 607/119
(58) Field of Search ............... 607/4, 5, 9, 36, 607/119

(56) References Cited

U.S. PATENT DOCUMENTS

| | | |
|---|---|---|
| 4,157,720 A | 6/1979 | Greatbatch |
| 4,223,678 A | 9/1980 | Langer et al. |
| 4,407,288 A | 10/1983 | Langer et al. |
| 4,603,705 A | 8/1986 | Speicher et al. |
| 4,830,005 A | 5/1989 | Woskow |
| 5,184,616 A | 2/1993 | Weiss |
| 5,331,966 A | 7/1994 | Bennett et al. |
| 5,366,496 A | 11/1994 | Dahl et al. |
| 5,376,103 A | 12/1994 | Anderson et al. |
| 5,411,539 A | 5/1995 | Neisz |
| 5,423,326 A | 6/1995 | Wang et al. |
| 5,645,586 A | 7/1997 | Meltzer |
| 5,843,132 A * | 12/1998 | Ilvento .................. 607/10 |
| 6,058,328 A | 5/2000 | Levine et al. |
| 6,093,173 A | 7/2000 | Balceta et al. |
| 6,144,879 A * | 11/2000 | Gray ........................ 607/20 |
| 6,266,567 B1 * | 7/2001 | Ishikawa et al. ............. 607/36 |
| 6,280,462 B1 * | 8/2001 | Hauser et al. ............... 607/5 |

FOREIGN PATENT DOCUMENTS

| | | |
|---|---|---|
| EP | 0 517 494 A3 | 12/1992 |
| EP | 0 517 494 A2 | 12/1992 |
| EP | 0 517 494 B1 | 12/1992 |
| EP | 0 627 237 A1 | 12/1994 |
| WO | WO 97/29802 A3 | 8/1997 |
| WO | WO 97/29802 A2 | 8/1997 |
| WO | WO 99/53991 A1 | 10/1999 |

OTHER PUBLICATIONS

International Search Report dated Mar. 26, 2002, PCT/US01/29168 filed Sep. 14, 2001, published as WO 02/22208 on Mar. 21, 2002, Subcutaneous Only Implantable Cardioverter Defibrlillator & Optional Pacer, Inventors: Gust H Bardy et al.

(List continued on next page.)

*Primary Examiner*—Jeffrey R. Jastrzab
(74) *Attorney, Agent, or Firm*—Gottlieb, Rackman & Reisman, P.C.

(57) ABSTRACT

A unitary subcutaneous implantable cardioverter-defibrillator is disclosed which has a long thin housing in the shape of a patient's rib. The housing contains a source of electrical energy, a capacitor, and operational circuitry that senses the presence of potentially fatal heart rhythms. Provided on the housing are cardioversion/defibrillation electrodes located to deliver electrical cardioversion-defibrillation energy when the operational circuitry senses a potentially fatal heart rhythm. The unitary subcutaneous implantable cardioverter-defibrillator does not have a transvenous, intracardiac, epicardial, or subcutaneous electrode.

104 Claims, 3 Drawing Sheets

OTHER PUBLICATIONS

Written Opinion dated Sep. 10, 2002, PCT/US01/29168 filed Sep. 14, 2001, published as WO 02/22208 on Mar. 21, 2002, Subcutaneous Only Implantable Cardioverter Defibrlillator & Optional Pacer, Inventors: Gust H Bardy et al.

International Search Report dated Mar. 21, 2002,, PCT/US01/29106 filed Sep. 14, 2001, published as WO 02/24275 on Mar. 28, 2002, Unitary Subcutaneous Only Implantable Cardioverter Defibrillator & Optional Pacer, Inventors: Gust H Bardy et al.

Written Opinion dated Sep. 3, 2002, PCT/US01/29106 filed Sep. 14, 2001, published as WO 02/24275 on Mar. 28, 2002, Unitary Subcutaneous Only Implantable Cardioverter Defibrillator & Optional Pacer, Inventors: Gust H Bardy et al.

Journal of the American Medical Association (JAMA), Vol 214, No 6, 1123pp, Nov. 9, 1970, "Completely Implanted Defibrillator", an editorial comment by JC Schuder PhD.

Amer Soc Trans Artif Int Organs, Vol XVI, 1970, 207–212pp, "Experimental Ventricular Defibrillation With An Automatic & Completely Implanted System", by JC Schuder PhD et al.

Archives of Internal Medicine (Specialized Journal of the AMA), Vol 127, Feb. 1971, Letters to the Editor 317pp, "Standby Implanted Defibrillators", an editirial comment by JC Schuder PhD.

Journal of the American Medical Association (JAMA), Vol 213, 615–616pp, 1970, "Automatic Detection & Defibrillation of Lethal Arrhythmias—A New Concept", by Mirkowski et al.

IEEE Transactions on Bio–Medical Engineering, Vol BME–18, No 6, Nov. 1971, 410–415pp, "Transthoracic Ventricular Defibrillation In The Dog With Truncated and Untruncated Exponential Stimuli", by JC Schuder PhD et al.

Pace, Vol 16, Part I, Jan. 1993, 95–124pp, "The Role Of An Engineering Oriented Medical Research Group In Developing Improved Methods & Devices For Achieving Ventricular Defibrillation: The University Of Missouri Experience", by JC Schuder PhD.

Journal of Cardiovascular Electrophysiology, Vol 12, No 3, Mar. 2001, 356–360pp, Copyright 2001, by Future Publishing Company Inc, Armonk–NY 1050–0418, "Nonthoracotomy Implantable Cardioverter Defibrillator Placement In Children", by Rainer Gradaus MD et al.

Journal of Cardiovascular Electrophysiology, Vol 12, No 3, Mar. 2001, 361–362pp, Copyright 2001, by Future Publishing Company Inc, Armonk–NY 1050–0418, "Implantable Defibrillators In Children: From Whence to Shock", by Richard A Friedman MD et al.

* cited by examiner

UNITARY SUBCUTANEOUS ONLY IMPLANTABLE CARDIOVERTER-DEFIBRILLATOR AND OPTIONAL PACER

CROSS REFERENCE TO RELATED APPLICATION

This patent application is related to U.S. patent application Ser. No. 09/663,607, filed Sep. 18, 2000, pending, the disclosure of which is incorporated by reference.

FIELD OF THE INVENTION

The present invention relates to an apparatus and method for performing electrical cardioversion/defibrillation and optional pacing of the heart via a totally subcutaneous non-transvenous system.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing.

Defibrillation/cardioversion systems include body implantable electrodes and are referred to as implantable cardioverter/defibrillators (ICDs). Such electrodes can be in the form of patches applied directly to epicardial tissue, or at the distal end regions of intravascular catheters, inserted into a selected cardiac chamber. U.S. Pat. Nos. 4,603,705, 4,693,253, 4,944,300, 5,105,810, the disclosures of which are all incorporated herein by reference, disclose intravascular or transvenous electrodes, employed either alone or in combination with an epicardial patch electrode. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat. No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has no practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led mnanufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353, 5,261,400, 5,620,477, and 5,658,321, the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, the requirement of ICD therapy to use intravenous catheters and transvenous leads is an impediment to very long term management as most individuals will begin to develop complications related to lead system malfunction sometime in the 5–10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of automatic external defibrillator (AED) therapy. AEDs employ the use of cutaneous patch electrodes to effect defibrillation under the direction of a bystander user who treats the patient suffering from V-Fib. AEDs can be as effective as an ICD if applied to the victim promptly within 2 to 3 minutes.

AED therapy has great appeal as a tool for diminishing the risk of death in public venues such as in air flight. However, an AED must be used by another individual, not the person suffering from the potentially fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years. We call such a device a unitary sub-cutaneous only ICD (US-ICD) and is described in detail below.

SUMMARY OF THE INVENTION

The preferred embodiment for the unitary subcutaneous only ICD (US-ICD) with optional pacing consists of five basic components: 1) a curved housing which houses a battery supply, capacitor, and operational circuitry; 2) two cardioversion/defibrillating electrodes are attached to the outer surface of the housing; 3) one or more sensing electrodes located on the housing; and 4) sense circuitry suitable to an ICD or AED V-FIB detection algorithm. Additionally, an application system is provided for simple insertion of the US-ICD. No transvenous lead system is used, eliminating a significant impediment to broader scale prophylactic use.

The housing will provide energy and voltage intermediate to that available with ICD and AEDs. The typical maximum voltage necessary for ICDs using most biphasic waveforms is approximately 750 V and associated maximum energy of approximately 40 J. The typical maximum voltage necessary for AEDs is approximately 2000–5000 V with an associated maximum energy of approximately 150–360 J. The US-ICD of the present invention will use voltages in the range of 800 to 2000 V and associated with energies of approximately 40–150 J.

The cardioversion/defibrillation electrodes are electrically insulated from each other and are about 5–10 cm length. In the preferred embodiment, the sense electrodes are located between the cardioversion/defibrillation electrodes and are spaced about 4 cm from each other to provide a reasonable QRS signal from a subcutaneous extracardiac sampling location but may be of variable length to allow for sense optimization.

The sense circuitry in the preferred embodiment is designed to be highly sensitive and specific to the presence or absence of life threatening ventricular arrhythmias only. Features of the detection algorithm are programmable but the algorithm is focused on the detection of V-Fib and high rate ventricular tachycardia (V-Tach) of greater than 240 bpm. This type of cardioverter-defibrillator is not necessarily designed to replace ICD therapy for those with pre-identified problems of V-Tach/V-Fib or even atrial fibrillation, but is particularly geared to use as a prophylactic, long-term device, used for the life of the patient at risk of his/her first V-Fib/V-Tach event. The device of the present invention may infrequently be used for an actual life threatening event but can be employed in large populations of individuals at modest risk and with modest cost by physicians of limited experience. Consequently, the preferred embodiment of the present invention focuses only on the detection and therapy of the most malignant rhythm disorders. As part of the detection algorithm's applicability to children, the upper rate range is programmable upward for use in children, who are known to have more rapid supraventricular tachycardias as well as more rapid ventricular tachycardias compared to adults.

The incision to apply the device of the present invention can be anywhere on the thorax although in the preferred embodiment, the device of the present invention will be applied in the anterior mid-clavicular line approximately at the level of the mammary crease beneath the left areolus. A subcutaneous path will then be made and will extend to the posterior thoracic region ideally at the level of the inferior scapula tip. Such a lead position will allow for a good transthoracic current delivery vector as well as positioning of the proximally positioned sense bipole in a good location for identification of the QRS ECG signal. A specially designed curved introducer set, through which local anesthetic can be delivered, is provided to assist in the placement of the US-ICD.

BRIEF DESCRIPTION OF THE DRAWINGS

For a better understanding of the invention, reference is now made to the drawings where like numerals represent similar objects throughout the figures where.

DESCRIPTION OF THE PREFERRED EMBODIMENTS

Figure 1:
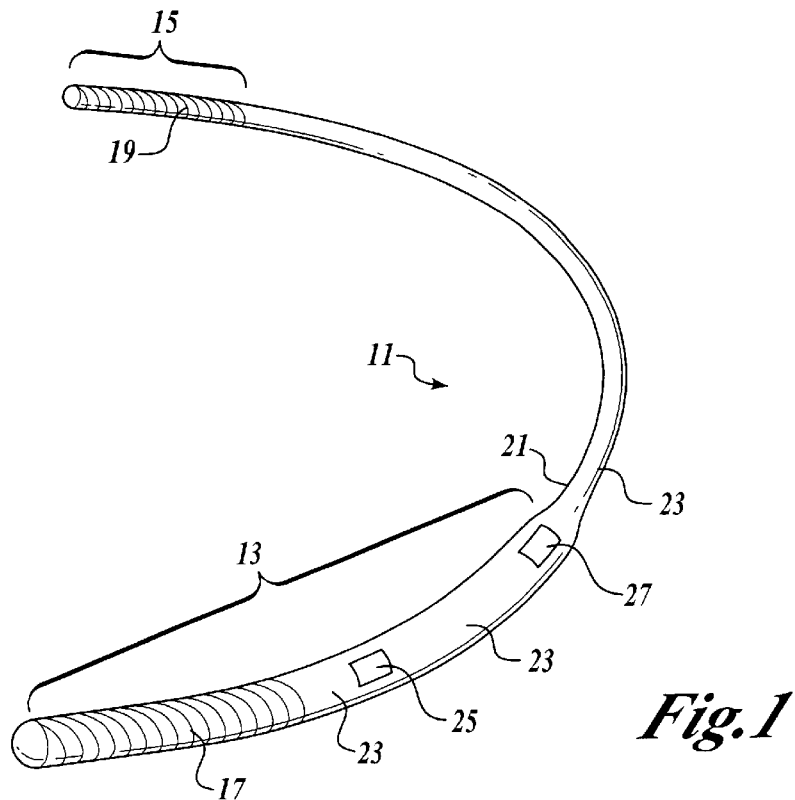
FIG. 1 is a schematic view of a Unitary Subcutaneous ICD (US-ICD) of the present invention.

Turning now to FIG. 1, the US-ICD of the present invention is illustrated. The US-ICD consists of a curved housing 11 with a first and second end. The first end 13 is thicker than the second end 15. This thicker area houses a battery supply, capacitor and operational circuitry for the US-ICD. The circuitry will be able to monitor cardiac rhythms for tachycardia and fibrillation, and if detected, will initiate charging the capacitor and then delivering cardioversion/defibrillation energy through the two cardioversion/defibrillating electrodes 17 and 19 located on the outer surface of the two ends of the housing. Examples of such circuitry are described in U.S. Pat. Nos. 4,693,253 and 5,105,810, the entire disclosures of which are herein incorporated by reference. The circuitry can provide cardioversion/defibrillation energy in different types of wave forms. In the preferred embodiment, a 100 uF biphasic wave form is used of approximately 10–20 ms total duration and with the initial phase containing approximately $\frac{2}{3}$ of the energy, however, any type of wave form can be utilized such as monophasic, biphasic, multiphasic or alternative waveforms as is known in the art.

In addition to providing cardioversion/defibrillation energy, the circuitry can also provide transthoracic cardiac pacing energy. The optional circuitry will be able to monitor the heart for bradycardia and/or tachycardia rhythms. Once a bradycardia or tachycardia rhythm is detected, the circuitry can then deliver appropriate pacing energy at appropriate intervals through the electrodes. Pacing stimuli will be biphasic in the preferred embodiment and similar in pulse amplitude to that used for conventional transthoracic pacing.

This same circuitry can also be used to deliver low amplitude shocks on the T-wave for induction of ventricular fibrillation for testing S-ICD performance in treating V-Fib as is described in U.S. Pat. No. 5,129,392, the entire disclosure of which is hereby incorporated by reference. Also the circuitry can be provided with rapid induction of ventricular fibrillation or ventricular tachycardia using rapid ventricular pacing. Another optional way for inducing ventricular fibrillation would be to provide a continuous low voltage, i.e. about 3 volts, across the heart during the entire cardiac cycle.

Another optional aspect of the present invention is that the operational circuitry can detect the presence of atrial fibrillation as described in Olson, W. et al. "Onset And Stability For Ventricular Tachyarrhythmia Detection in an Implantable Cardioverter and Defibrillator, Computers in Cardiology (1986) pp 167–170. Detection can be provided via R-R Cycle length instability detection algorithms. Once atrial fibrillation has been detected, the operational circuitry will then provide QRS synchronized atrial defibrillation/cardioversion using the same shock energy and waveshape characteristics used for ventricular defibrillation/cardioversion.

The sensing circuitry will utilize the electronic signals generated from the heart and will primarily detect QRS waves. In one embodiment, the circuitry will be programmed to detect only ventricular tachycardias or fibrillations. The detection circuitry will utilize in its most direct form, a rate detection algorithm that triggers charging of the capacitor once the ventricular rate exceeds some predetermined level for a fixed period of time: for example, if the ventricular rate exceeds 240 bpm on average for more than 4 seconds. Once the capacitor is charged, a confirmatory rhythm check would ensure that the rate persists for at least another 1 second before discharge. Similarly, termination algorithms could be instituted that ensure that a rhythm less than 240 bpm persisting for at least 4 seconds before the capacitor charge is drained to an internal resistor. Detection, confirmation and termination algorithms as are described above and in the art can be modulated to increase sensitivity and specificity by examining QRS beat-to-beat uniformity, QRS signal frequency content, R-R interval stability data, and signal amplitude characteristics all or part of which can be used to increase or decrease both sensitivity and specificity of S-ICD arrhythmia detection function.

In addition to use of the sense circuitry for detection of V-Fib or V-Tach by examining the QRS waves, the sense circuitry can check for the presence or the absence of respiration. The respiration rate can be detected by monitoring the impedance across the thorax using subthreshold currents delivered across the active can and the high voltage subcutaneous lead electrode and monitoring the frequency in undulation in the waveform that results from the undulations of transthoracic impedance during the respiratory cycle. If there is no undulation, then the patient is not respiring and this lack of respiration can be used to confirm the QRS findings of cardiac arrest. The same technique can be used to provide information about the respiratory rate or estimate cardiac output as described in U.S. Pat. Nos. 6,095,987, 5,423,326, 4,450,527, the entire disclosures of which are incorporated herein by reference.

The housing of the present invention can be made out of titanium alloy or other presently preferred ICD designs. It is contemplated that the housing is also made out of biocompatible plastic materials that electronically insulate the electrodes from each other. However, it is contemplated that a malleable canister that can conform to the curvature of the patient's chest will be preferred. In this way the patient can have a comfortable canister that conforms to the unique shape of the patient's rib cage. Examples of conforming ICD housings are provided in U.S. Pat. No. 5,645,586, the entire disclosure of which is herein incorporated by reference. In the preferred embodiment, the housing is curved in the shape of a $5^{th}$ rib of a person. Because there are many different sizes of people, the housing will come in different incremental sizes to allow a good match between the size of the rib cage and the size of the US-ICD. The length of the US-ICD will range from about 15 to about 50 cm. Because of the primary preventative role of the therapy and the need to reach energies over 40 Joules, a feature of the preferred embodiment is that the charge time for the therapy, intentionally be relatively long to allow capacitor charging within the limitations of device size.

The thick end of the housing is currently needed to allow for the placement of the battery supply, operational circuitry, and capacitors. It is contemplated that the thick end will be about 0.5 cm to about 2 cm wide with about 1 cm being presently preferred. As microtechnology advances, the thickness of the housing will become smaller. Examples of small ICD housings are disclosed in U.S. Pat. Nos. 5,957, 956 and 5,405,363, the entire disclosures of which are herein incorporated by reference.

The two cardioversion/defibrillation electrodes on the housing are used for delivering the high voltage cardioversion/defibrillation energy across the heart. In the preferred embodiment, the cardioversion/defibrillation electrodes are coil electrodes, however, other cardioversion/defibrillation electrodes could be used such as having electrically isolated active surfaces or platinum alloy electrodes. The coil cardioversion/defibrillation electrodes are about 5–10 cm in length. Located on the housing between the two cardioversion/defibrillation electrodes are two sense electrodes 25 and 27. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 23. Analogous types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is to have the sense electrodes at the two ends of the housing and have the cardioversion/defibrillation electrodes located in between the sense electrodes. Another modification is to have three or more sense electrodes spaced throughout the housing and allow for the selection of the two best sensing electrodes. If three or more sensing electrodes are used, then the ability to change which electrodes are used for sensing would be a programmable feature of the US-ICD to adapt to changes in the patient physiology and size over time. The programming could be done via the use of physical switches on the canister, or as presently preferred, via the use of a programming wand or via a wireless connection to program the circuitry within the canister.

The housing will provide energy and voltage intermediate to that available with ICDs and most AEDs. The typical maximum voltage necessary for ICDs using most biphasic waveforms is approximately 750 Volts with an associated maximum energy of approximately 40 Joules. The typical maximum voltage necessary for AEDs is approximately 2000–5000 Volts with an associated maximum energy of approximately 200–360 Joules depending upon the model and waveform used. The US-ICD of the present invention uses maximum voltages in the range of about 800 to about 2000 Volts and is associated with energies of about 40 to about 150 Joules. The capacitance of the S-ICD could range from about 50 to about 200 micro farads.

The sense circuitry contained within the housing is highly sensitive and specific for the presence or absence of life threatening ventricular arrhythmias. Features of the detection algorithm are programmable and the algorithm is focused on the detection of V-FIB and high rate V-TACH (>240 bpm). Although the US-ICD of the present invention may rarely be used for an actual life threatening event, the simplicity of design and implementation allows it to be employed in large populations of patients at modest risk with modest cost by non-cardiac electrophysiologists. Consequently, the US-ICD of the present invention focuses mostly on the detection and therapy of the most malignant rhythm disorders. As part of the detection algorithm's applicability to varying patient populations, the detection rate range is programmable upward or downward to meet the needs of the particular patient based on their cardiac condition and age.

Figure 2:
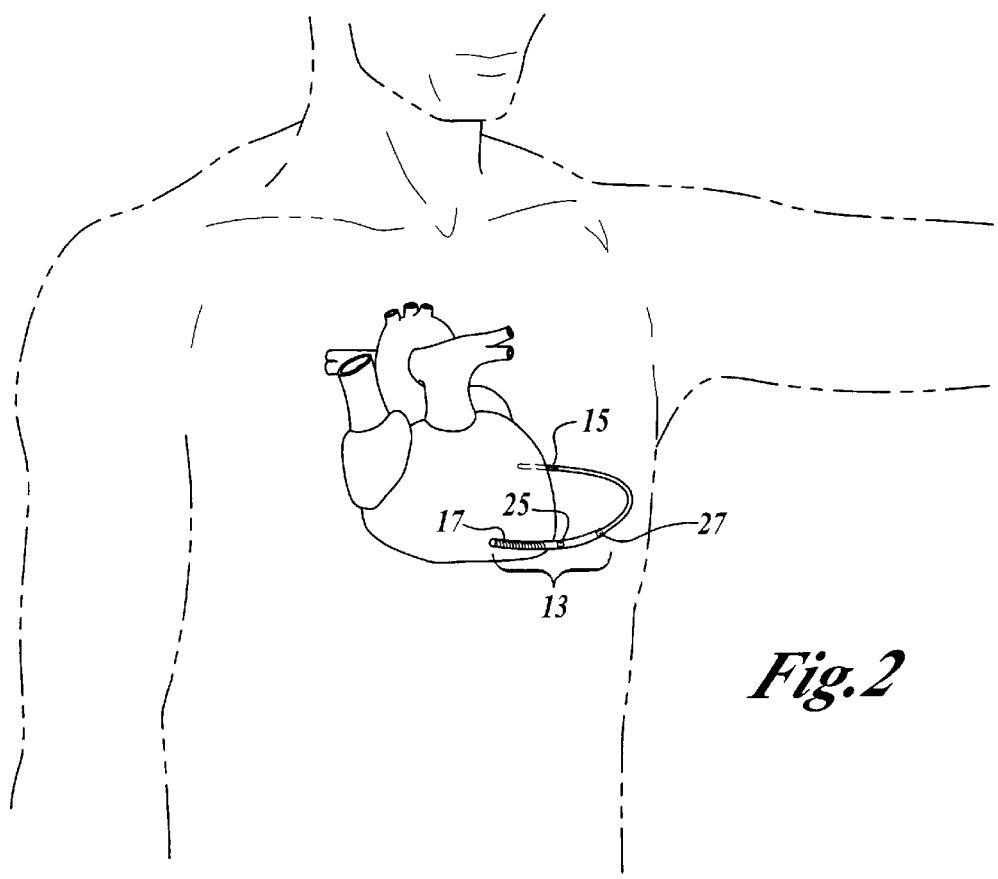
FIG. 2 is a schematic view of the US-ICD subcutaneously implanted in the thorax of a patient.

Turning now to FIG. 2, the optimal subcutaneous placement of the US-ICD of the present invention is illustrated. As would be evident to a person skilled in the art, the actual location of the US-ICD is in a subcutaneous space that is developed during the implantation process. The heart is not exposed during this process and the heart is schematically illustrated in the figures only for help in understanding where the device and its various electrodes are three dimensionally located in the thorax of the patient. The US-ICD is located between the left mid-clavicular line approximately at the level of the inframammary crease at approximately the $5^{th}$ rib and the posterior axillary line, ideally just lateral to the left scapula. This way the US-ICD provides a reasonably good pathway for current delivery to the majority of the ventricular myocardium.

Figure 3:
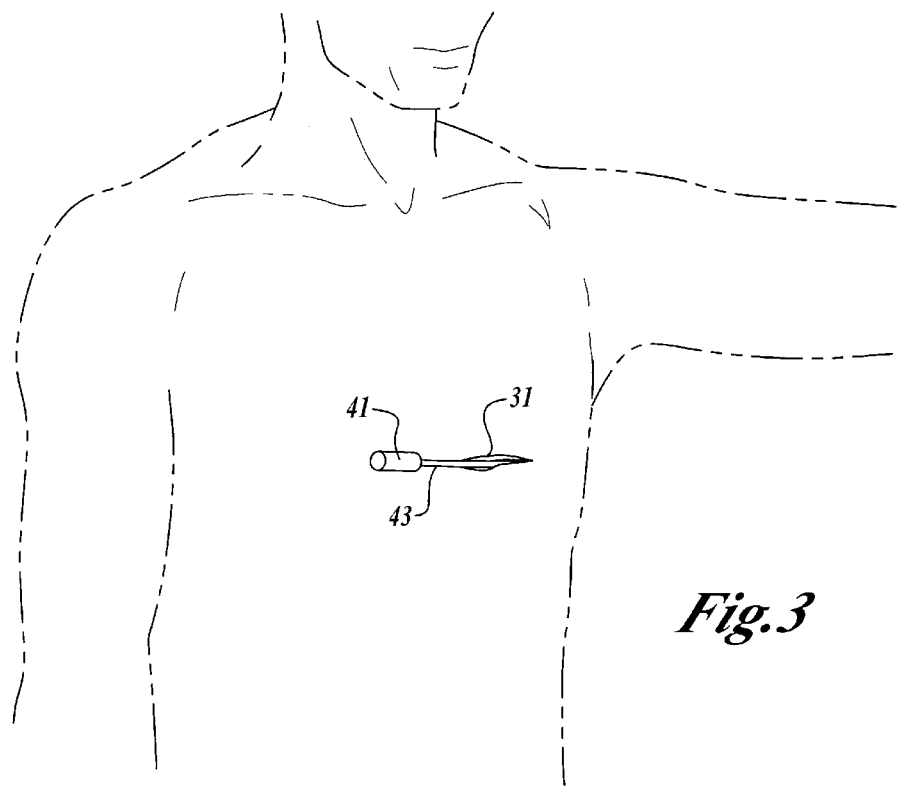
FIG. 3 is a schematic view of the method of making a subcutaneous path from the preferred incision for implanting the US-ICD.
Figure 4:
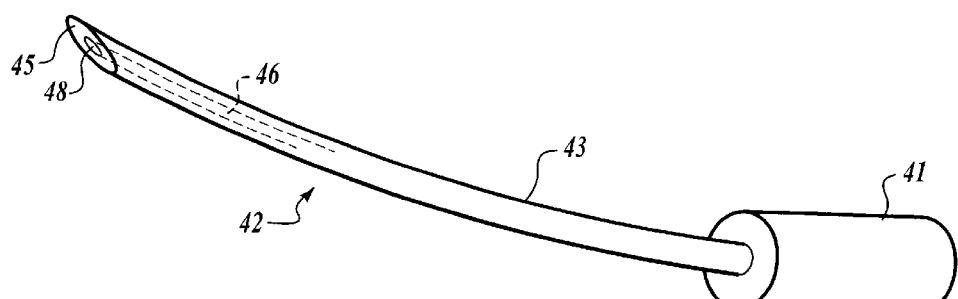
FIG. 4 is a schematic view of an introducer for performing the method of US-ICD implantation.

FIG. 3 schematically illustrates the method for implanting the US-ICD of the present invention. An incision 31 is made in the left anterior axillary line approximately at the level of the cardiac apex. A subcutaneous pathway 33 is then created that extends posteriorly to allow placement of the US-ICD. The incision can be anywhere on the thorax deemed reasonable by the implanting physician although in the preferred embodiment, the US-ICD of the present invention will be applied in this region. The subcutaneous pathway 33 is created medially to the inframammary crease and extends posteriorly to the left posterior axillary line. The pathway is developed with a specially designed curved introducer 40 (see FIG. 4). The trocar has a proximal handle 41 and a curved shaft 43. The distal end 45 of the trocar is tapered to allow for dissection of the subcutaneous pathway 33 in the patient. Preferably, the trocar is cannulated having a central lumen 46 and terminating in an opening 48 at the distal end. Local anesthetic such as lidocaine can be delivered, if necessary, through the lumen or though a curved and elongated needle designed to anesthetize the path to be used for trocar insertion should general anesthesia not be employed. Once the subcutaneous pathway is developed, the US-ICD is implanted in the subcutaneous space, the skin incision is closed using standard techniques.

Figure 5:
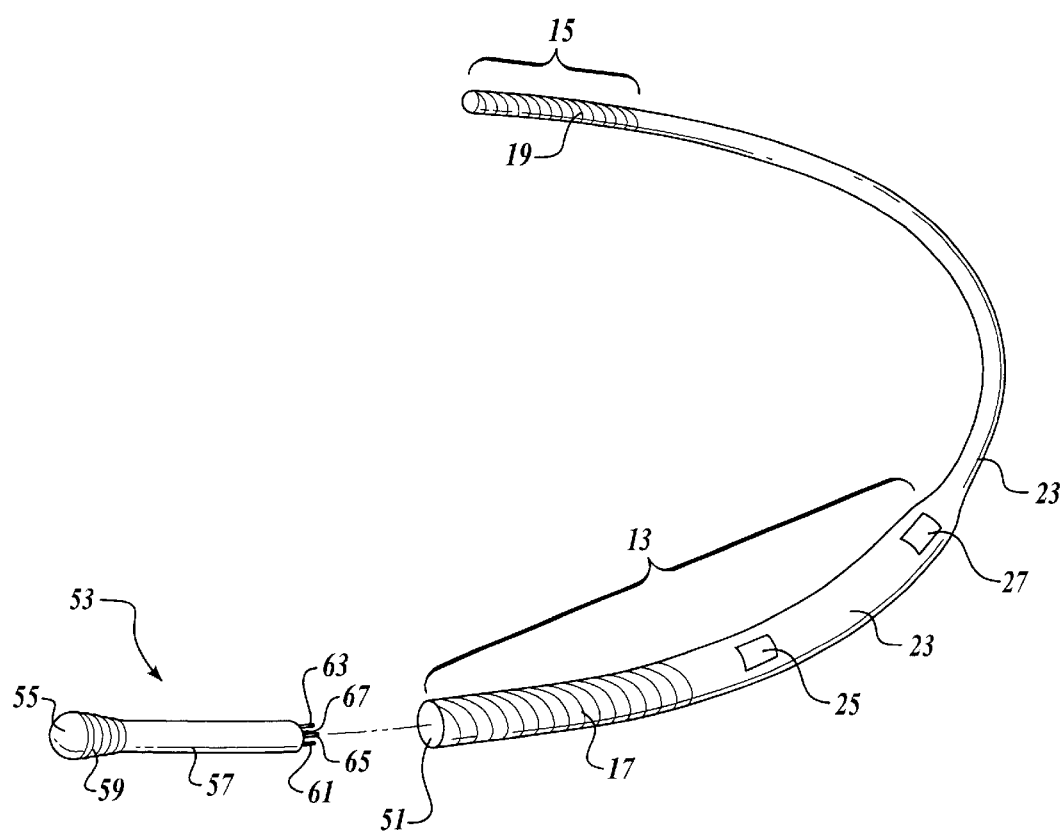
FIG. 5 is an exploded schematic view of an alternate embodiment of the present invention with a plug-in portion that contains operational circuitry and means for generating cardioversion/defibrillation shock waves.

As described previously, the US-ICDs of the present invention vary in length and curvature. The US-ICDs are provided in incremental sizes for subcutaneous implantation in different sized patients. Turning now to FIG. 5, a different embodiment is schematically illustrated in exploded view which provides different sized US-ICDs that are easier to manufacture. The different sized US-ICDs will all have the same sized and shaped thick end 13. The thick end is hollow inside allowing for the insertion of a core operational member 53. The core member comprises a housing 57 which contains the battery supply, capacitor and operational circuitry for the US-ICD. The proximal end of the core member has a plurality of electronic plug connectors. Plug connectors 61 and 63 are electronically connected to the sense electrodes via pressure fit connectors (not illustrated) inside the thick end which are standard in the art. Plug connectors 65 and 67 are also electronically connected to the cardioverter/defibrillator electrodes via pressure fit connectors inside the thick end. The distal end of the core member comprises an end cap 55, and a ribbed fitting 59 which creates a water-tight seal when the core member is inserted into opening 51 of the thick end of the US-ICD.

The core member of the different sized and shaped US-ICD will all be the same size and shape. That way, during an implantation procedures, multiple sized US-ICDs can be available for implantation, each one without a core member. Once the implantation procedure is being performed, then the correct sized US-ICD can be selected and the core member can be inserted into the US-ICD and then programmed as described above. Another advantage of this configuration is when the battery within the core member needs replacing it can be done without removing the entire US-ICD.

The US-ICD device and method of the present invention may be embodied in other specific forms without departing from the teachings or essential characteristics of the invention. The described embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

What is claimed is:

1. A unitary subcutaneous implantable cardioverter-defibrillator comprising:
    a long thin housing with first and second ends that is curved in a shape of a patient's rib wherein the housing contains a source of electrical energy, a capacitor, and operational circuitry that senses the presence of potentially fatal heart rhythms;
    cardioversion/defibrillation electrodes located at the ends of the housing;
    means for delivering electrical cardioversion-defibrillation energy when the operational circuitry senses a potentially fatal heart rhythm; and
    the absence of a transvenous, intracardiac, or epicardial, electrode.

2. The unitary subcutaneous implantable cardioverter-defibrillator of claim 1 wherein the electrical cardioversion-defibrillating energy is equal to or greater than 800 Volts.

3. The unitary subcutaneous implantable cardioverter-defibrillator of claim 2 wherein the electrical cardioversion-defibrillating energy ranges from about 800 volts to about 2000 volts.

4. The unitary subcutaneous implantable cardioverter-defibrillator of claim 1 wherein the electrical cardioversion-defibrillating energy ranges from about 40 Joules to about 150 Joules.

5. The unitary subcutaneous implantable cardioverter-defibrillator of claim 1 further comprising at least two sensing electrodes located on the housing.

6. The unitary subcutaneous implantable cardioverter-defibrillator of claim 5 wherein the sensing electrodes are spaced apart by about 1 to about 10 cm.

7. The unitary subcutaneous implantable cardioverter-defibrillator of claim 6 wherein the first and second sensing electrodes are spaced apart by about 4 cm.

8. The unitary subcutaneous implantable cardioverter-defibrillator of claim 1 wherein the operational circuitry can also sense the presence of bradycardia rhythm.

9. The unitary subcutaneous implantable cardioverter-defibrillator of claim 8 further comprising means for delivering cardiac pacing energy when the operational circuitry senses a bradycardia rhythm.

10. The unitary subcutaneous implantable cardioverter-defibrillator of claim 1 wherein the operational circuitry is programmable.

11. The unitary subcutaneous implantable cardioverter-defibrillator of claim 1 wherein the operational circuitry can detect tachycardia.

12. The unitary subcutaneous implantable cardioverter-defibrillator of claim 11 further comprising means for delivering antitachycardia pacing when the operational circuitry senses a tachycardia rhythm.

13. The unitary subcutaneous implantable cardioverter-defibrillator of claim 11 wherein the ventricular tachycardia detected is greater than 240 beats per minute.

14. The unitary subcutaneous implantable cardioverter-defibrillator of claim 1 wherein the operational circuitry can detect atrial tachycardia and atrial fibrillation.

15. The unitary subcutaneous implantable cardioverter-defibrillator of claim 14 wherein the operational circuitry can deliver defibrillation energy to treat the detected atrial fibrillation.

16. The unitary subcutaneous implantable cardioverter-defibrillator of claim 1 wherein the operational circuitry can induce ventricular tachycardia or ventricular fibrillation.

17. The unitary subcutaneous implantable cardioverter-defibrillator of claim 16 wherein the ventricular tachycardia or ventricular fibrillation is induced by shocks on the T wave.

18. The unitary subcutaneous implantable cardioverter-defibrillator of claim 16 wherein the ventricular tachycardia or ventricular fibrillation is induced by low direct current voltage applied during the entire cardiac cycle.

19. The unitary subcutaneous implantable cardioverter-defibrillator of claim 1 wherein the electrical cardioversion-defibrillating energy is delivered in a biphasic wave form.

20. The unitary subcutaneous implantable cardioverter-defibrillator of claim 1 wherein the capacitance is about 50 to about 200 micro farads.

21. The unitary subcutaneous implantable cardioverter-defibrillator of claim 1 wherein the housing is malleable.

22. The unitary subcutaneous implantable cardioverter-defibrillator of claim 1 wherein the housing is provided with at least one sensing electrode.

23. The unitary subcutaneous implantable cardioverter-defibrillator of claim 1 wherein the housing is provided with one or more sensing electrodes, and wherein said cardioverter-defibrillator is further provided with a subcutaneous electrode with one or more sensing electrodes, and means for selecting two sensing electrodes from the sensing electrodes located on the housing and the sensing electrode located on the subcutaneous electrode that provide adequate QRS wave detection.

24. The unitary subcutaneous implantable cardioverter-defibrillator of claim 1 wherein the electrical cardioversion-defibrillating energy is delivered for about 10 to about 20 milliseconds total duration and with the initial positive phase containing approximately $2/3$ of the energy delivered.

25. The unitary subcutaneous implantable cardioverter-defibrillator of claim 1 wherein the operational circuitry comprises an impedance detection for measuring the undulations in transthoracic impedance created during respiration.

26. The unitary subcutaneous implantable cardioverter-defibrillator of claim 25 wherein the operational circuitry can also measure the cardiac output using transthoracic impedance.

27. The unitary subcutaneous implantable cardioverter-defibrillator of claim 1 wherein the housing ranges in length from about 15 to about 20 cm.

28. The unitary subcutaneous implantable cardioverter-defibrillator of claim 27 wherein the unitary subcutaneous implantable cardioverter-defibrillator is provided in different incremental sizes.

29. The unitary subcutaneous implantable cardioverter-defibrillator of claim 1 further comprising a plug-in core member inside the housing of the unitary subcutaneous implantable cardioverter-defibrillator wherein the plug-in core member contains the source of electrical energy, the capacitor, and the operational circuitry.

30. The unitary subcutaneous implantable cardioverter-defibrillator of claim 29 wherein the housing ranges in length from about 15 to about 20 cm.

31. The unitary subcutaneous implantable cardioverter-defibrillator of claim 29 wherein the unitary subcutaneous implantable cardioverter-defibrillator is provided in different incremental sizes.

32. A method of implanting a unitary implantable subcutaneous cardioverter-defibrillator in a patient comprising the steps of;

making only one skin incision in the thoracic region of the patient;

inserting a curved introducer through the skin incision to make a subcutaneous path in the thoracic region such that the path terminates subcutaneously at an end location that if a straight line were drawn from the skin incision to the end location, the line would intersect the heart of the patient;

implanting a unitary subcutaneous cardioverter-defibrillator that has a long thin housing that is curved in a shape of a patient's rib; and closing the skin incision.

33. The method of implanting a subcutaneous cardioverter-defibrillator of claim 32 further comprising the step of injecting a local anesthetic through the curved introducer.

34. The method of implanting a subcutaneous cardioverter-defibrillator of claim 32 wherein the skin incision is located in the left anterior axillary line approximately at the level of the patient's cardiac apex.

35. A unitary cardioverter-defibrillator for subcutaneous implantation, comprising:

a canister comprising a biocompatible housing enclosing and containing cardioversion-defibrillation circuitry, said housing having a downward taper continuously formed along at least one exterior periphery of the biocompatible housing; and a pair of electrodes formed on opposite ends of the biocompatible housing and electrically interfaced to the cardioversion-defibrillation circuitry to deliver an electrical therapy to the heart of a patient.

36. A unitary cardioverter-defibrillator according to claim 35, further comprising:

at least one sensing electrode formed on, and electrically insulated from, the biocompatible housing and electrically interfaced to the cardioversion-defibrillation circuitry.

37. A unitary cardioverter-defibrillator according to claim 35, further comprising:

at least one electrically insulated surface defined on an outer surface of the biocompatible housing and juxtaposed to the pair of electrodes.

38. A unitary cardioverter-defibrillator according to claim 37, further comprising:

at least one sensing electrode formed on the at least one electrically insulated surface and electrically interfaced to the cardioversion-defibrillation circuitry.

39. A unitary cardioverter-defibrillator according to claim 37, further comprising:

an insulated margin around at least one of the pair of electrodes along the at least one electrically insulated surface and defining a concentrated electrically conductive surface.

40. A unitary cardioverter-defibrillator according to claim 37, wherein the at least one electrically insulated surface is constructed from at least one of a silicon, polyurethane, ceramic, titanium-ceramic bonded, Parylene-coated, and other biocompatible material.

41. A unitary cardioverter-defibrillator according to claim 35, further comprising:
monitoring circuitry integral to the cardioversion-defibrillation circuitry and deriving physiological measures relating to at least one of QRS signal morphology, QRS signal frequency content, QRS R-R interval stability data, and QRS amplitude characteristics.

42. A unitary cardioverter-defibrillator according to claim 35, further comprising:
a pulse generator integral to the cardioversion-defibrillation circuitry and producing an anti-arrhythmia waveform for anti-arrhythmia therapy via the pair of electrodes responsive to the cardioversion-defibrillation circuitry.

43. A unitary cardioverter-defibrillator according to claim 42, further comprising:
the pulse generator generating the anti-arrhythmia waveform as a biphasic waveform with characteristics comprising at least one of a capacitance between approximately 50 $\mu$F and 200 mF, voltage between approximately 800 V and 2000 V, energy between 40 J and 150 J, and a duration between approximately 5 msec to 25 msec.

44. A unitary cardioverter-defibrillator according to claim 43, further comprising:
the cardioversion-defibrillation circuitry initiating the anti-arrhythmia therapy upon a cardiac ventricular rate of around 240 bpm sustained over an at least 4 second interval.

45. A unitary cardioverter-defibrillator according to claim 43, further comprising:
the cardioversion-defibrillation circuitry confirming the anti-arrhythmia therapy upon a cardiac ventricular rate of around 240 bpm sustained over an approximately 1 second interval.

46. A unitary cardioverter-defibrillator according to claim 43, further comprising:
the cardioversion-defibrillation circuitry terminating the anti-arrhythmia therapy upon a cardiac ventricular rate of around 240 bpm sustained over an at least 4 second interval.

47. A unitary cardioverter-defibrillator according to claim 43, further comprising:
power supply components integral to the cardioversion-defibrillation circuitry, consisting essentially of four or more batteries and four or more capacitors and providing power sufficient to generate the anti-arrhythmia waveform.

48. A unitary cardioverter-defibrillator according to claim 35, further comprising:
pacing circuitry operatively conjunctive to the cardioversion-defibrillation circuitry which generates at least one of an anti-bradycardia and an anti-tachycardia pacing waveform via the pair of electrodes responsive to the cardioversion-defibrillation circuitry.

49. A unitary cardioverter-defibrillator according to claim 35, further comprising:
induction circuitry integral to the cardioversion-defibrillation circuitry which generates low amplitude voltage on a T-wave of an ECG via the pair of electrodes responsive to the cardioversion-defibrillation circuitry.

50. A unitary cardioverter-defibrillator according to claim 35, further comprising:
a pair of semi-converging tapers continuously formed about opposite sides of the downward taper.

51. A unitary cardioverter-defibrillator according to claim 50, further comprising:
at least one surface of the biocompatible housing formed in at least one of a curved and non-linear surface.

52. A unitary cardioverter-defibrillator according to claim 51, further comprising:
the at least one surface formed as a radian bend curving continuously approximately axial to the biocompatible housing.

53. A unitary cardioverter-defibrillator according to claim 35, further comprising:
at least one of a fractalized and a wrinkled surface formed on the outer surface of the biocompatible housing.

54. A unitary cardioverter-defibrillator according to claim 35, wherein the biocompatible housing is constructed from at least one of a titanium alloy and another biocompatible material, such other material being malleable.

55. A unitary cardioverter-defibrillator according to claim 35, further comprising:
monitoring circuitry integral to the cardioversion-defibrillation circuitry and obtaining physiological measures via the pair of electrodes.

56. A unitary cardioverter-defibrillator according to claim 35, further comprising:
each of the pair of electrodes formed non-circumferentially on the biocompatible housing and with an overall electrically active component of less than approximately 10 $cm^2$.

57. A unitary cardioverter-defibrillator according to claim 35, further comprising:
each of the pair of electrodes interfacing with high voltage and low impedance circuitry.

58. A unitary cardioverter-defibrillator according to claim 57, further comprising:
a plurality of sensing electrodes formed on the biocompatible housing, each sensing electrode interfacing with low voltage and high impedance circuitry.

59. A unitary cardioverter-defibrillator according to claim 58, further comprising:
each such sensing electrode formed on opposite ends of the biocompatible housing.

60. A unitary cardioverter-defibrillator according to claim 58, further comprising:
each such sensing electrode formed between the pair of electrodes.

61. A unitary cardioverter-defibrillator according to claim 58, further comprising:
at least one such sensing electrode formed non-circumferentially on the biocompatible housing.

62. A unitary cardioverter-defibrillator for subcutaneous implantation, comprising:
a canister comprising a biocompatible housing enclosing and containing cardioversion-defibrillation circuitry; and
a pair of electrodes formed on opposite ends of the biocompatible housing and electrically interfaced to the cardioversion-defibrillation circuitry to deliver an electrical therapy to the heart of a patient;
wherein said canister has two ends, one end being a thicker end within which the cardioversion-defibrillation circuitry is contained.

63. A unitary cardioverter-defibrillator according to claim 62, further comprising:
a core operational member containing the cardioversion-defibrillation circuitry separate from the biocompatible housing; and a hollow recess formed within the biocompatible housing operationally disposed to receive the core operational member.

64. A unitary cardioverter-defibrillator according to claim 63, further comprising:
a plurality of connectors matchingly formed on a proximal end of the core operational member and on the distal end of the hollow recess, each connector interfacing the cardioversion-defibrillation circuitry to the pair of electrodes.

65. A unitary cardioverter-defibrillator according to claim 63, further comprising:
an endcap with ribbed fittings formed along a proximal end of the core operational member and hermetically fitting within the hollow recess.

66. A unitary cardioverter-defibrillator for subcutaneous implantation, comprising:
a canister comprising a biocompatible housing enclosing and containing cardioversion-defibrillation circuitry; and
a pair of electrodes formed on opposite ends of the biocompatible housing and electrically interfaced to the cardioversion-defibrillation circuitry to deliver an electrical therapy to the heart of a patient;
wherein the biocompatible housing has one of several incremental sizes.

67. A unitary cardioverter-defibrillator for subcutaneous implantation, comprising:
a canister comprising a biocompatible housing enclosing and containing cardioversion-defibrillation circuitry; and
a pair of electrodes formed on opposite ends of the biocompatible housing and electrically interfaced to the cardioversion-defibrillation circuitry to deliver an electrical therapy to the heart of a patient;
wherein the biocompatible housing is shaped conformal to the rib cage.

68. A unitary cardioverter-defibrillator for subcutaneous implantation, comprising:
a canister comprising a biocompatible housing enclosing and containing cardioversion-defibrillation circuitry; and
a pair of electrodes formed on opposite ends of the biocompatible housing and electrically interfaced to the cardioversion-defibrillation circuitry to deliver an electrical therapy to the heart of a patient;
wherein the biocompatible housing is further formed conformal to at least one of the fourth, fifth and sixth anterior rib spaces of a patient.

69. A unitary subcutaneous cardioverter-defibrillator with electrically active canister for minimally invasive implantation, comprising:
a subcutaneously implantable canister comprising a sterilizable biocompatible housing enclosing and containing cardioversion-defibrillation circuitry interfaceable through the biocompatible housing, the biocompatible housing formed into a partially curved surface along a longitudinal axis, with a downward taper continuously formed along an exterior periphery of the biocompatible housing, and a pair of semi-converging tapers continuously formed about opposite sides of the downward taper; and
a pair of electrodes formed on opposite and facing ends of the biocompatible housing and electrically interfaced via one or more internal conductors to the cardioversion-defibrillation circuitry to deliver an electrical therapy to the heart of a patient therebetween.

70. A unitary subcutaneous cardioverter-defibrillator according to claim 69, further comprising:
the pair of electrodes further interfacing with sensing circuitry and providing a sensing function to the cardioversion-defibrillation circuitry.

71. A unitary subcutaneous cardioverter-defibrillator according to claim 69, further comprising:
at least one of the pair of electrodes formed as a concentrated electrically conductive surface defined about a surface of the biocompatible housing and facing the heart when implanted.

72. A unitary subcutaneous cardioverter-defibrillator according to claim 69, further comprising
at least one electrically insulated surface defined about a surface of the biocompatible housing facing away from the heart and juxtaposed to the pair of electrodes.

73. A unitary subcutaneous cardioverter-defibrillator according to claim 72, further comprising:
an insulating area substantially interposed between the pair of electrodes and the at least one electrically insulated surface.

74. A unitary subcutaneous cardioverter-defibrillator according to claim 69, further comprising:
at least one sensing electrode formed on, and electrically insulated from, the pair of electrodes and electrically interfaced to the cardioversion-defibrillation circuitry, each sensing electrode interfacing with sensing circuitry and providing a sensing function to the cardioversion-defibrillation circuitry.

75. A unitary subcutaneous cardioverter-defibrillator according to claim 74, further comprising:
an electrically insulated surface about each at least one sensing electrode abutting the biocompatible housing and marginal to the pair of electrodes.

76. A unitary subcutaneous cardioverter-defibrillator according to claim 74, further comprising:
each of the sensing electrodes formed in locations comprising at least one of a location between the pair of electrodes and outside the pair of electrodes.

77. A unitary subcutaneous cardioverter-defibrillator according to claim 74, further comprising:
at least one such sensing electrode formed non-circumferentially along an interior surface of the biocompatible housing.

78. A unitary subcutaneous cardioverter-defibrillator according to claim 69, wherein at least one surface of the biocompatible housing forms a continuous radian curve.

79. A unitary subcutaneous cardioverter-defibrillator according to claim 69, further comprising:
a pulse generator integral to the cardioversion-defibrillation circuitry and generating an antiarrhythmia biphasic waveform with characteristics comprising at least one of a capacitance between approximately 50 $\mu$F and 200 $\mu$F, voltage between approximately 800 V and 2000 V, energy between 40 J and 150 J, and a duration between approximately 5 msec to 25 msec.

80. A unitary subcutaneous cardioverter-defibrillator according to claim 69, further comprising:
the cardioversion-defibrillation circuitry comprising at least one of:
monitoring circuitry deriving physiological measures relating to at least one of QRS signal morphology, QRS signal frequency content, QRS R-R interval stability data, and QRS amplitude characteristics;

a pulse generator producing an anti-arrhythmia waveform for anti-arrhythmia therapy via the pair of electrodes responsive to the cardioversion-defibrillation circuitry;

pacing circuitry operatively conjunctive to the cardioversion-defibrillation circuitry which generates at least one of an anti-bradycardia and an anti-tachycardia pacing waveform via the pair of electrodes responsive to the cardioversion-defibrillation circuitry; and induction circuitry generating low amplitude voltage on a T-wave of an ECG via the pair of electrodes responsive to the cardioversion-defibrillation circuitry.

81. A unitary subcutaneous cardioverter-defibrillator according to claim 69, wherein the biocompatible housing is constructed from at least one of a titanium alloy and another biocompatible material, such another material being malleable.

82. A unitary subcutaneous cardioverter-defibrillator with electrically active canister for minimally invasive implantation, comprising:

a subcutaneously implantable canister comprising a sterilizable biocompatible housing enclosing and containing cardioversion-defibrillation circuitry interfaceable through the biocompatible housing, the biocompatible housing formed into a partially curved surface along a longitudinal axis; and a pair of electrodes formed on opposite and facing ends of the biocompatible housing and electrically interfaced via one or more internal conductors to the cardioversion-defibrillation circuitry to deliver an electrical therapy to the heart of a patient therebetween;

wherein a thicker end is defined on one end of the canister, said thicker end being sized to contain the cardioversion-defibrillation circuitry exclusive of the remainder of the canister.

83. A unitary subcutaneous cardioverter-defibrillator according to claim 82 further comprising:

self-contained power supply components contained within the biocompatible housing and integral to the cardioversion-defibrillation circuitry, consisting essentially of four or more batteries and four or more capacitors and providing power sufficient to generate the anti-arrhythmia biphasic waveform.

84. A unitary subcutaneous cardioverter-defibrillator with electrically active canister for minimally invasive implantation, comprising:

a subcutaneously implantable canister comprising a sterilizable biocompatible housing enclosing and containing cardioversion-defibrillation circuitry interfaceable through the biocompatible housing, the biocompatible housing formed into a partially curved surface along a longitudinal axis; and a pair of electrodes formed on opposite and facing ends of the biocompatible housing and electrically interfaced via one or more internal conductors to the cardioversion-defibrillation circuitry to deliver an electrical therapy to the heart of a patient therebetween;

further comprising:

a removable core member containing the operational circuitry separate from the biocompatible housing and providing a plurality of electronic connectors; and the biocompatible housing operationally disposed to receive the core operational member via a plurality of matching electronic connectors.

85. A unitary cardioversion-defibrillation device with electrically conductive housing means for subcutaneous implantation, comprising:

means for housing and hermetically containing cardioversion-defibrillation circuitry, the housing means defining a curved and substantially electrically insulated outer surface, with a downward taper continuously formed along an exterior periphery of the housing means, and a pair of semi-converging tapers continuously formed about opposite sides of the downward taper; and means for delivering an electrical therapy from opposite and facing ends of the housing means responsive to an autonomously detected arrhythmic condition, the electrical therapy delivering means being electrically connected via one or more internal conductors to the cardioversion-defibrillation circuitry.

86. A unitary cardioversion-defibrillation device according to claim 85, further comprising:

means for monitoring and deriving physiological measures relating to at least one of QRS signal morphology, QRS signal frequency content, QRS R-R interval stability data, and QRS amplitude characteristics;

means for producing an anti-arrhythmia waveform for anti-arrhythmia therapy via the electrical therapy delivering means responsive to the cardioversion-defibrillation circuitry;

means for pacing circuitry operatively conjunctive to the cardioversion-defibrillation circuitry which generates at least one of an anti-bradycardia and an anti-tachycardia pacing waveform via the electrical therapy delivering means responsive to the cardioversion-defibrillation circuitry; and means for induction circuitry generating low amplitude voltage on a T-wave of an ECG via the electrical therapy delivering means responsive to the cardioversion-defibrillation circuitry.

87. A unitary cardioversion-defibrillation device according to claim 85, further comprising:

sensing means provided via the electrical therapy delivering means, the sensing means being electrically connected via the one or more internal conductors to the cardioversion-defibrillation circuitry to interface with sensing circuitry.

88. A unitary cardioversion-defibrillation device according to claim 85, further comprising:

sensing means provided abutting and electrically insulated from the housing means, the sensing means being electrically connected via the one or more internal conductors to the cardioversion-defibrillation circuitry to interface with sensing circuitry.

89. A subcutaneous cardioverter-defibrillator according to claim 88, further comprising:

each of the sensing means formed in locations comprising at least one of a location between the electrical therapy delivering means and outside the electrical therapy delivering means.

90. A unitary cardioversion-defibrillation device according to claim 85, further comprising:

at least one electrically insulated surface defined about a surface of the housing means facing the heart and juxtaposed to the electrical therapy delivering means.

91. A unitary cardioversion-defibrillation device according to claim 85, further comprising:

pulse generating means integral to the cardioversion-defibrillation circuitry and generating an anti-arrhythmia biphasic waveform with characteristics comprising at least one of a capacitance between approximately 50 µF and 200 µF, voltage between approximately 800 V and 2000 V, energy between 40 J and 150 J, and a duration between approximately 5 msec to 25 msec.

92. A unitary cardioversion-defibrillation device according to claim 85, further comprising:

a radian bend continuously formed approximately axial to the housing means.

93. A unitary cardioversion-defibrillation device according to claim 85, further comprising:

operational means containing the cardioversion-defibrillation circuitry separate from the housing means and providing-means for connecting along a proximal end; and receiving means formed within a distal end of the housing means operationally disposed to receive the operational means via the connecting means.

94. A unitary cardioversion-defibrillation device according to claim 85, wherein the housing means is constructed from at least one of a titanium alloy and another biocompatible material, such another material being malleable.

95. An implantable unitary subcutaneous cardioverter-defibrillator with electrically active canister, comprising:

an implantable canister providing a curved housing enclosing and containing cardioversion-defibrillation circuitry;

a pair of electrodes formed on opposite and facing ends of the housing and electrically interfaced via one or more conductors to the cardioversion-defibrillation circuitry to deliver an electrical therapy to the heart of a patient responsive to an autonomously detected arrhythmic condition; and a removable core operational member containing the cardioversion-defibrillation circuitry separate and interchangeably from the housing and providing a plurality of connectors, the housing being operationally disposed to receive the core operational member via a plurality of matching connectors.

96. An implantable unitary subcutaneous cardioverter-defibrillator according to claim 95, further comprising:

an electrically insulated surface juxtaposed to the pair of electrodes and substantially interposed therefrom by an electrically insulated area.

97. An implantable unitary subcutaneous cardioverter-defibrillator according to claim 95, further comprising:

a plurality of sensing electrodes formed on the housing and electrically connected with the one or more conductors to the cardioversion-defibrillation circuitry, each of the sensing electrodes interfacing with sensing circuitry within the cardioversion-defibrillation circuitry and providing a sensing function.

98. An implantable unitary subcutaneous cardioverter-defibrillator according to claim 97, further comprising:

each of the sensing electrodes formed on locations along the, housing comprising at least one of a surface of the implantable canister facing the heart and a surface of the implantable canister facing toward the skin.

99. An implantable unitary subcutaneous cardioverter-defibrillator according to claim 95, further comprising:

an anti-arrhythmic pulse generator integral to the cardioversion-defibrillation circuitry and generating an anti-arrhythmia biphasic waveform between the pair of electrodes with characteristics comprising at least one of a capacitance between approximately 50 µF and 200 µF, voltage between approximately 800 V and 2000 V, energy between 40 J and 150 J, and a duration between approximately 5 msec to 25 msec.

100. An implantable unitary subcutaneous cardioverter-defibrillator with electrically active canister, comprising:

an implantable canister providing a curved housing enclosing and containing cardioversion-defibrillation circuitry;

a pair of electrodes formed on opposite and facing ends of the housing and electrically interfaced via one or more conductors to the cardioversion-defibrillator circuitry to deliver an electrical therapy to the heart of a patient responsive to an autonomously detected arrhythmic condition;

a removable core operational member containing the cardioversion-defibrillation circuitry separate and interchangeably from the housing and providing a plurality of connectors, the housing operationally disposed to receive the core operational member via a plurality of matching connectors.

101. A method for providing anti-arrhythmia therapy via a unitary subcutaneous cardioverter-defibrillator, comprising:

implanting a canister comprising a curved biocompatible housing subcutaneously in a patient in the anterior thorax approximately level with the inframammary crease and extending posteriorly towards the left posterior axillary line, the biocompatible housing enclosing and containing cardioversion-defibrillation circuitry and defining a pair of electrodes on the outer surface of the biocompatible housing that faces the heart and electrically connected to the cardioversion-defibrillation circuitry; and delivering an electrical therapy comprising an anti-arrhythmia waveform to the heart of a patient from the pair of electrodes.

102. A method according to claim 101, the method further comprising: implanting the canister in a region proximate to at least one of the fourth, fifth and sixth anterior rib spaces of a patient.

103. A method according to claim 101, the method further comprising: providing a plurality of sensing electrodes formed on the canister, electrically isolated from the pair of electrodes, each sensing electrode interfacing with sensing circuitry to the cardioversion-defibrillation circuitry; and monitoring and deriving cardiac physiological measures relating to at least one of QRS signal morphology, QRS signal frequency content, QRS R-R interval stability data, and QRS amplitude characteristics via the sensing electrodes.

104. A method according to claim 101, further comprising:

generating low amplitude voltage on a T-wave of an ECG via the pair of electrodes responsive to the cardioversion-defibrillation circuitry.

* * * * *

UNITED STATES PATENT AND TRADEMARK OFFICE
CERTIFICATE OF CORRECTION

| | |
|---|---|
| PATENT NO. | : 6,647,292 B1 |
| DATED | : November 11, 2003 |
| INVENTOR(S) | : Gust H. Bardy et al. |

It is certified that error appears in the above-identified patent and that said Letters Patent is hereby corrected as shown below:

Column 10,
Line 2, delete "claim 29", and insert therefor -- claim 30 --.

Signed and Sealed this

Twentieth Day of July, 2004

JON W. DUDAS
*Acting Director of the United States Patent and Trademark Office*